United States Patent [19]

Bailey

[11] Plant 4,397

[45] Mar. 20, 1979

[54] ROSE PLANT

[75] Inventor: Dorothy J. S. Bailey, Bakersfield, Calif.

[73] Assignee: San Joaquin Rose Co., McFarland, Calif.

[21] Appl. No.: 903,221

[22] Filed: May 5, 1978

[51] Int. Cl.[2] ..... A01H 5/00

[52] U.S. Cl. ..... Plt./19

[58] Field of Search ..... Plt./19-20

*Primary Examiner*—Robert E. Bagwill
*Attorney, Agent, or Firm*—Vincent G. Gioia

[57] ABSTRACT

A novel rose variety of the hybrid tea class characterized by very large flowers of strong red coloring, borne singly on a strong stem as shown and described herein.

1 Drawing Figure

1

The present invention relates to a new and distinct variety of rose plant of the hybrid tea class, which was originated by my crossing the rose variety known as "First Prize" as seed parent with the rose variety known as "Mr. Lincoln" as pollen parent.

Among the novel characteristics possessed by this new variety which distinguish it from its parents and all other varieties of which I am aware are: (1) very large flowers of dark red coloring which change to deep velvety purple upon aging, (2) long pointed buds opening into flowers of high center which are very long lasting on the plant, and (3) a very vigorous plant with very thick petals and abundant, large foliage of leathery texture. Asexual reproduction by budding of the new variety as performed in Kern County, Calif., shows that the foregoing and other distinguishing characteristics come true to form and are established and transmitted through succeeding propagations.

A main distinguishing feature of the new and improved rose variety is its unusual, large, dark red flowers which are produced on sturdy stems. In addition, this new variety does not possess the same susceptibility to diseases, such as "mildew", which is typical of many red roses.

Flowers of this new variety are usually borne singly, opening as high centered buds and maintaining the high center affect as it ages. Petals are very thick and have a velvety inside and are regularly arranged, however, the flowers are long lasting on the plant and after cutting. The large, abundant, thick, leathery foliage provides good support for these unusually large flowers.

The accompanying drawing shows typical specimens of the flowers and vegetative growth of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.
*Seed parent.*—"First Prize".
*Pollen Parent.*—"Mr. Lincoln".
Class: Hybrid tea.

2

The following observations are made of specimens grown outdoors at Kern County, Calif., during the month of June.

1. FLOWER

Blooming habit: Continuous

A. Bud:
- (1) *Size.*—Very large.
- (2) *Form.*—Long pointed, full.
- (3) *Color.*—When sepals first divide: Near 53B. When petals begin to unfurl: 53C. When half-blown: Inside of petals — 53D. Reverse side of petals — 53C.
- (4) *Sepals.*—Notched, relatively short, extending about two-thirds the length of the bud.
- (5) *Peduncle.*—Length — 3 to 3½ inches. Aspect — stiff, smooth. Strength — Erect. Color — 183B.

B. Bloom:
- (1) *Size.*—Average size when fully expanded 5–6 inches.
- (2) *Borne.*—Singly.
- (3) *Form.*—High centered.
- (4) *Petalage.*—Number of petals under normal conditions — about 48.
- (5) *Color.*—Center of flower — 53D. Outer petals — 53D. Reverse of petals — 53B. General tonality from a distance — 53C, deepening to 57C upon aging and finally to deep velvety purple (57B) after three or more days.

C. Petals:
- (1) *Texture.*—Very thick.
- (2) *Appearance.*—Inside — velvety; outside — satiny.
- (3) *Form.*—Fan shaped, pointed at base.
- (4) *Arrangement.*—regularly arranged, shingle-like.
- (5) *Petaloids in center.*—Medium.
- (6) *Persistence.*—Drop off clean.
- (7) *Fragrance.*—Strong, old rose fragrance.
- (8) *Lasting quality.*—Very long lasting on the plant and as a cut flower.

2. REPRODUCTIVE ORGANS

A. Stamens, anthers:
- (1) *Arrangement.*—Regularly arranged around styles.
- (2) *Color.*—20B.

B. Pollen: Color — 22C.

C. Styles: Bunches; medium length.

D. Stigmas: Color — 58B.

E. Hips:

*Shape.*—Globular, large.

*Color.*—33B when mature, seeds protrude.

3. PLANT

A. Form: Spreading and upright.

B. Growth: Very vigorous.

C. Foliage: Compound of 5 to 7 leaves.

(1) *Size.*—Large.

(2) *Quantity.*—Abundant.

(3) *Color.*—New foliage: upper side — 60B with green undertones; under side — 60D. Old foliage: upper side — 139A; under side — 139B.

(4) *Shape.*—Oval to pointed.

(5) *Texture.*—Upper side — dull, leathery. Under side — rough, veined.

(6) *Edge.*—Smooth.

(7) *Serration.*—None.

(8) *Leaf stem.*—Color — 147B; under side — 147C.

(9) *Stipules.*—Medium length.

D. Wood:

(1) *New Wood.*—Color — 183C. Bark — smooth.

(2) *Old Wood.*—Color — 183A. Bark — smooth.

E. Thorns:

(1) *Thorns.*—Quantity: on main stalks from base — medium; on laterals from stalk — few. Form: Flat. Length: Medium. Color when young — 185B. Position: Irregular.

(2) *Prickles.*—Quantity: on main stalks — substantial; on laterals — profuse.

F. Plant's disease resistance: Mildew — excellent. Blackspot — excellent. Rust — none observed.

G. Winter hardiness: Very winter hardy.

I claim:

1. A new and distinct variety of rose plant of the hybrid tea class, substantially as shown and described, characterized particularly by very large flowers of strong red coloring developing from long pointed buds and borne singly on strong stems and a very vigorous plant with large leathery foliage very resistant to disease and very winter hardy.

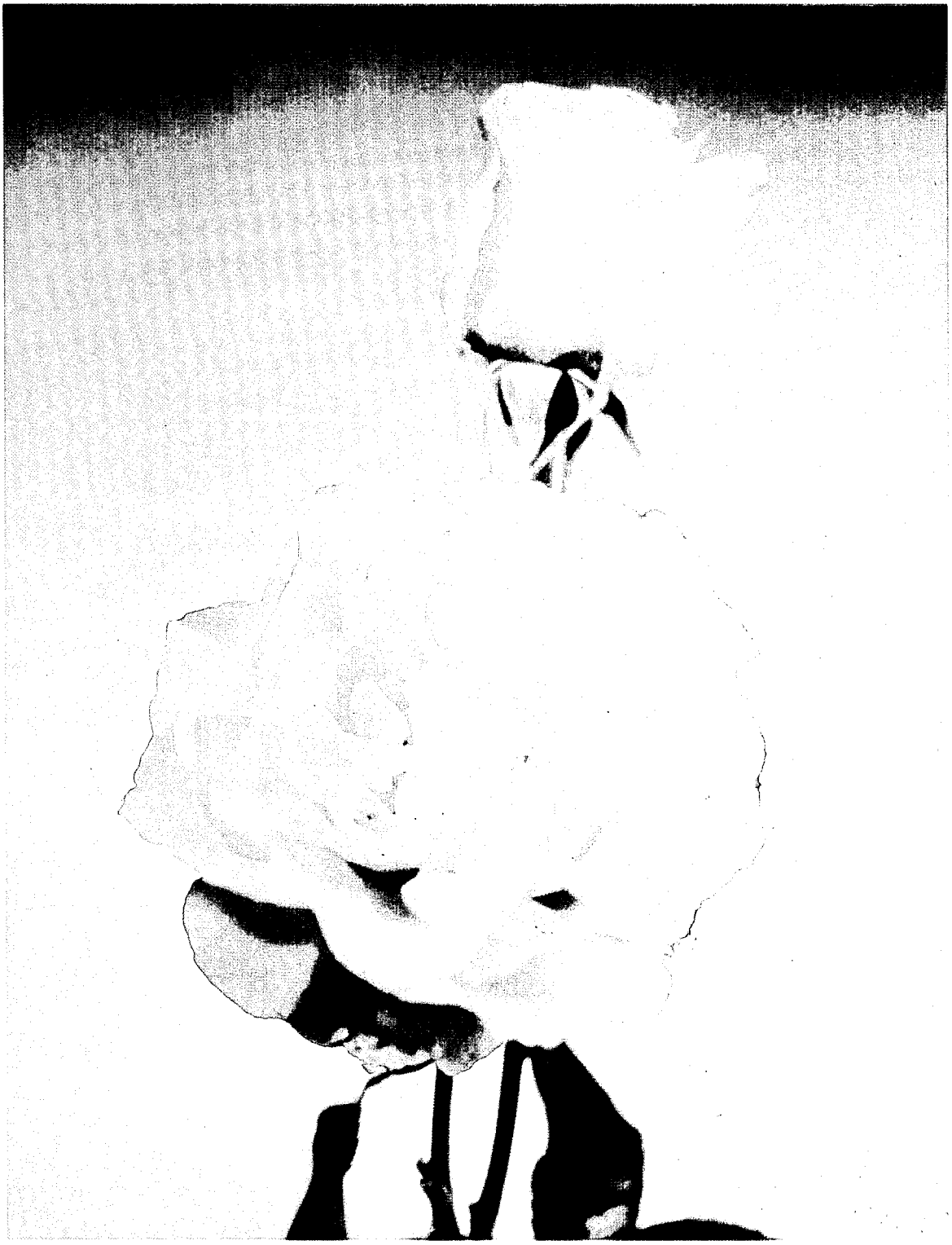

* * * * *